(12) United States Patent
Murata et al.

(10) Patent No.: US 11,427,701 B2
(45) Date of Patent: Aug. 30, 2022

(54) CHLOROPRENE COPOLYMER LATEX COMPOSITION AND MOLDED PRODUCT THEREOF

(71) Applicant: SHOWA DENKO K.K., Tokyo (JP)

(72) Inventors: Tomoaki Murata, Tokyo (JP); Noriko Ogawa, Tokyo (JP); Masanao Kamijo, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 17/276,537

(22) PCT Filed: Sep. 26, 2018

(86) PCT No.: PCT/JP2018/035783
§ 371 (c)(1),
(2) Date: Mar. 16, 2021

(87) PCT Pub. No.: WO2020/065789
PCT Pub. Date: Apr. 2, 2020

(65) Prior Publication Data
US 2022/0033626 A1 Feb. 3, 2022

(51) Int. Cl.
| | | |
|---|---|---|
| *C08L 11/02* | (2006.01) | |
| *A61B 42/10* | (2016.01) | |
| *A41D 19/00* | (2006.01) | |
| *C08K 3/22* | (2006.01) | |
| *C08K 5/00* | (2006.01) | |
| *C08K 5/13* | (2006.01) | |
| *C08K 5/31* | (2006.01) | |
| *C08K 5/405* | (2006.01) | |

(52) U.S. Cl.
CPC .......... *C08L 11/02* (2013.01); *A41D 19/0062* (2013.01); *A61B 42/10* (2016.02); *C08K 3/22* (2013.01); *C08K 5/005* (2013.01); *C08K 5/0025* (2013.01); *C08K 5/13* (2013.01); *C08K 5/31* (2013.01); *C08K 5/405* (2013.01); *A41D 2500/50* (2013.01); *C08K 2003/2296* (2013.01)

(58) Field of Classification Search
CPC ..................................................... C08L 11/02
See application file for complete search history.

(56) References Cited

U.S. PATENT DOCUMENTS

| | | | | |
|---|---|---|---|---|
| 3,397,173 | A * | 8/1968 | Collette | .................. C08L 11/02 |
| | | | | 524/349 |
| 4,605,705 | A | 8/1986 | Takeshita | |
| 6,195,805 | B1 * | 3/2001 | Bourne | ................. A61L 31/049 |
| | | | | 2/161.7 |
| H2092 | H * | 12/2003 | Bauman | ....................... 523/102 |
| 2012/0021155 | A1 | 1/2012 | Chen et al. | |
| 2012/0022195 | A1 | 1/2012 | Miyauchi et al. | |
| 2020/0199260 | A1 * | 6/2020 | Nishino | .................... C08F 2/38 |

FOREIGN PATENT DOCUMENTS

| | | |
|---|---|---|
| JP | 60-31510 A | 2/1985 |
| JP | 61-72011 A | 4/1986 |
| JP | 1-185309 A | 7/1989 |
| JP | 3-215538 A | 9/1991 |
| JP | 2003-55409 A | 2/2003 |
| JP | 2007-106994 A | 4/2007 |
| JP | 4238686 B2 | 3/2009 |
| JP | 2011-122141 A | 6/2011 |
| JP | 2013-534555 A | 9/2013 |
| JP | 2015-218225 A | 12/2015 |
| WO | 2010/095591 A1 | 8/2010 |

OTHER PUBLICATIONS

Machine translation of JP 2007106994 (2007, pages).*
International Search Report for PCT/JP2018/035783 dated Nov. 20, 2018 (PCT/ISA/210).
International Preliminary Report on Patentability dated Mar. 23, 2021 with translation of Written Opinion in International Application No. PCT/JP2018/035783.

* cited by examiner

*Primary Examiner* — Brieann R Johnston

(57) ABSTRACT

There is provided a chloroprene copolymer latex composition capable of obtaining a molded product having excellent mechanical properties and flexibility even when vulcanized and molded under milder conditions than before. A chloroprene copolymer latex composition contains a chloroprene copolymer latex (A), a metal oxide (B), a vulcanization accelerator (C), and an antioxidant (D). The chloroprene copolymer latex (A) is a latex containing particles of a chloroprene copolymer which is a copolymer of chloroprene (A-1), 2,3-dichloro-1,3-butadiene (A-2), and sulfur (A-3). The content of the sulfur (A-3) in the chloroprene copolymer is 0.1 part by mass or more and 1.0 part by mass or less when the total amount of the chloroprene (A-1) and the 2,3-dichloro-1,3-butadiene (A-2) is set to 100 parts by mass.

14 Claims, No Drawings

CHLOROPRENE COPOLYMER LATEX COMPOSITION AND MOLDED PRODUCT THEREOF

CROSS REFERENCE TO RELATED APPLICATIONS

This application is a National Stage of International Application No. PCT/JP2018/035783 filed Sep. 26, 2018.

TECHNICAL FIELD

The present invention relates to a chloroprene copolymer latex composition and a molded product thereof.

BACKGROUND ART

Chloroprene rubber which has flexibility and mechanical properties close to those of natural rubber and which is relatively inexpensive has been used as a raw material of medical disposable gloves, particularly surgical gloves. However, conventional chloroprene rubber has an insufficient polymer structure, and therefore has been required to be vulcanized at a high temperature or for a long period of time in order to obtain vulcanized rubber having target strength. Therefore, when dipped products, such as gloves, are manufactured by a dip processing method using a chloroprene rubber latex, the production efficiency has been low and the energy cost required for the production has been high.

It is known that sulfur-modified chloroprene rubber in which sulfur is copolymerized among the chloroprene rubber has a high vulcanization speed. However, the sulfur-modified chloroprene rubber has had a problem that, when dipped products are manufactured using a sulfur-modified chloroprene rubber latex, flexibility required in the surgical gloves is hard to obtain. Further, the sulfur-modified chloroprene rubber latex also has had a problem of being hard to be industrially used due to insufficient storage stability thereof.

For example, PTL 1 discloses a technology of improving the storage stability of the chloroprene rubber latex. For example, PTL 2 and PTL 3 disclose technologies of improving the mechanical properties or the flexibility of the chloroprene rubber. However, the temperature condition or the processing time condition in a vulcanization step (crosslinking step) has not been sufficiently reduced, and thus the vulcanization step has required a high temperature or a long period of time.

CITATION LIST

Patent Literature

PTL 1: JP 04238686
PTL 2: JP 2015-218225 A
PTL 3: JP 2007-106994 A

SUMMARY OF INVENTION

Technical Problem

It is an object of the present invention to solve the problems of the conventional technologies described above and to provide a chloroprene copolymer latex composition capable of obtaining a molded product having excellent mechanical properties and flexibility even when vulcanized and molded under milder conditions than before. Further, it is also an object of the present invention to provide a molded product having excellent mechanical properties and flexibility obtained by molding the chloroprene copolymer latex composition.

Solution to Problem

In order to solve the above-described problems, one aspect of the present invention is as described in [1] to [7] below.

[1] A chloroprene copolymer latex composition contains a chloroprene copolymer latex (A), a metal oxide (B), a vulcanization accelerator (C), and an antioxidant (D), in which the chloroprene copolymer latex (A) is a latex containing particles of a chloroprene copolymer which is a copolymer of chloroprene (A-1), 2,3-dichloro-1,3-butadiene (A-2), and sulfur (A-3), and the content of the sulfur (A-3) in the chloroprene copolymer is 0.1 part by mass or more and 1.0 part by mass or less when the total amount of the chloroprene (A-1) and the 2,3-dichloro-1,3-butadiene (A-2) is set to 100 parts by mass.

[2] The chloroprene copolymer latex composition according to [1], in which, with respect to the copolymerization ratio of the chloroprene (A-1) and the 2,3-dichloro-1,3-butadiene (A-2) in the chloroprene copolymer, the chloroprene (A-1) is 76% by mass or more and 93% by mass or less and the 2,3-dichloro-1,3-butadiene (A-2) is 24% by mass or less and 7% by mass or more when the total amount of the chloroprene (A-1) and the 2,3-dichloro-1,3-butadiene (A-2) is set to 100% by mass.

[3] The chloroprene copolymer latex composition according to [1] or [2], in which, when the amount of the solid content in the chloroprene copolymer latex (A) is set to 100 parts by mass, the amount of the metal oxide (E) is 1 part by mass or more and 10 parts by mass or less, the amount of the vulcanization accelerator (C) is 0.1 part by mass or more and 5 parts by mass or less, and the amount of the antioxidant (D) is 0.1 part by mass or more and 5 parts by mass or less.

[4] A molded product, which is the chloroprene copolymer latex composition according to any one of [1] to [3], in which the 300% modulus of elasticity is 0.5 MPa or more and 1.6 MPa or less, the tensile strength is 18 MPa or more, and the tensile elongation at break is 800% or more.

[5] The molded product according to [4], which is a dipped product.

[6] The molded product according to [5], which is a glove.

[7] The molded product according to [5], which is a medical disposable glove.

Advantageous Effects of Invention

The chloroprene copolymer latex composition according to the present invention can obtain a molded product having excellent mechanical properties and flexibility even when vulcanized and molded under milder conditions than before. Further, a molded product according to the present invention has excellent mechanical properties and flexibility.

DESCRIPTION OF EMBODIMENTS

One embodiment of the present invention will now be described below. A chloroprene copolymer latex composition according to this embodiment contains a chloroprene copolymer latex (A), a metal oxide (B), a vulcanization accelerator (C), and an antioxidant (D). The chloroprene copolymer latex (A) is a latex containing particles of a chloroprene copolymer which is a copolymer of chloroprene (A-1), 2,3-dichloro-1,3-butadiene (A-2), and sulfur (A-3).

The content of the sulfur (A-3) in the chloroprene copolymer is 0.1 part by mass or more and 1.0 part by mass or less when the total amount of the chloroprene (A-1) and the 2,3-dichloro-1,3-butadiene (A-2) is set to 100 parts by mass. When the content of the sulfur (A-3) is 0.1 part by mass or more, the crosslinking reactivity of the chloroprene copolymer latex composition is excellent. Therefore, even when the chloroprene copolymer latex composition is vulcanized and molded under milder conditions than before (for example, lower temperature and/or shorter processing time than before), a molded product having excellent mechanical properties and flexibility can be obtained. Further, when the content of the sulfur (A-3) is 1.0 part by mass or less, a polymerization reaction or the chloroprene (A-1), the 2,3-dichloro-1,3-butadiene (A-2), and the sulfur (A-3) is not inhibited, so that the degree of polymerization conversion increases. In order to further improve such effects, the content of the sulfur (A-3) in the chloroprene copolymer is more preferably set to 0.2 part by mass or more and 0.4 part by mass or less when the total amount of the chloroprene (A-1) and the 2,3-dichloro-1,3-butadiene (A-2) is set to 100 parts by mass.

The content of a tetrahydrofuran insoluble content in the chloroprene copolymer may be set to 50% by mass or more and 85% by mass or less.

Further, when the amount of the solid content in the chloroprene copolymer latex (A) is set to 100 parts by mass, the amount of the metal oxide (B) may be set to 1 part by mass or more and 10 parts by mass or less, the amount of the vulcanization accelerator (C) may be set to 0.1 part by mass or more and 5 parts by mass or less, and the amount of the antioxidant (D) may be set to 0.1 part by mass or more and 5 parts by mass or less in the chloroprene copolymer latex composition according to this embodiment.

In the chloroprene copolymer latex composition according to this embodiment, when the content of the tetrahydrofuran insoluble content in the chloroprene copolymer is controlled as described above, the effect that a molded product having excellent mechanical properties and flexibility can be obtained is improved even when the chloroprene copolymer latex composition according to this embodiment is vulcanized and molded under milder conditions than before (for example, lower temperature and/or shorter processing time than before).

Hence, the use of the chloroprene copolymer latex composition according to this embodiment enables a reduction in the thermal energy amount required for the vulcanization, and therefore the molded product of the chloroprene copolymer can be produced with high productivity at a low cost.

Further, 2,3-dichloro-1,3-butadiene is compounded as a copolymerization component of the chloroprene copolymer in the chloroprene copolymer latex composition according to this embodiment, and therefore a molded product having excellent flexibility can be obtained.

When the chloroprene copolymer latex composition according to this embodiment is molded, a molded product can be obtained in which the 300% modulus of elasticity (modulus of elasticity at 300% elongation) is 0.5 MPa or more and 1.6 MPa or less, the tensile strength is 18 MPa or more, and the tensile elongation at break is 800% or more.

Further, dipped products can be obtained by molding the chloroprene copolymer latex composition according to this embodiment by a dip processing method. Examples of molded products obtained by the dip processing method include gloves, balloons, sphygmomanometer bladders, and thread rubber, for example. Examples of the gloves include medical disposable gloves.

Hereinafter, the chloroprene copolymer latex composition according to this embodiment and the molded product thereof are described in more detail. This embodiment describes an example of the present invention and the present invention is not limited to this embodiment. Further, this embodiment can be variously altered or modified and embodiments obtained by such alternations or modifications are also included in the present invention.

[1] Chloroprene (A-1)

The chloroprene as a main raw material monomer of the chloroprene copolymer which is one component of the chloroprene copolymer latex composition according to this embodiment is a compound also referred to as 2-chloro-1, 3-butadiene or 2-chlorobutadiene.

[2] Chloroprene Copolymer and Chloroprene Copolymer Latex (A)

The chloroprene copolymer which is one component of the chloroprene copolymer latex composition according to this embodiment is a copolymer of the chloroprene (A-1), the 2,3-dichloro-1,3-butadiene (A-2), and the sulfur (A-3). The 2,3-dichloro-1,3-butadiene (A-2) has good copolymerizability with the chloroprene (A-1). By the copolymerization ratio, the properties of the chloroprene copolymer, such as the crystallization resistance, eventually flexibility, are easily adjusted.

The copolymerization ratio of the chloroprene (A-1) and the 2,3-dichloro-1,3-butadiene (A-2) in the chloroprene copolymer is not particularly limited. When the total amount of the chloroprene (A-1) and the 2,3-dichloro-1,3-butadiene (A-2) is set to 100% by mass, the chloroprene (A-1) may be set to 76% by mass or more and 93% by mass or less and the 2,3-dichloro-1,3-butadiene (A-2) may be set to 24% by mass or less and 7% by mass or more.

When the proportion of the 2,3-dichloro-1,3-butadiene (A-2) is 7% by mass or more, the stability of the flexibility with time of the chloroprene copolymer is improved. When the proportion is 24% by mass or less, crystallization of the chloroprene copolymer is suppressed and the flexibility is improved. In order to further improve such effects, the proportion of the 2,3-dichloro-1,3-butadiene (A-2) is more preferably set to 15% by mass or less and 10% by mass or more.

In the chloroprene copolymer, "other monomers (A-4)" other than the chloroprene (A-1), the 2,3-dichloro-1,3-butadiene (A-2), and the sulfur (A-3) may be copolymerized insofar as the objects of the present invention are not impaired. Examples of the other monomers (A-4) include 1-chloro-1,3-butadiene, butadiene, isoprene, styrene, acrylonitrile, acrylic acid and an ester compound thereof, and methacrylic acid and an ester compound thereof. The other monomers (A-4) may be used alone or may be used in combination of two or more types.

The use amount of the other monomers (A-4) is not particularly limited and can be set in the range of 0.1 part by mass or more and 10 parts by mass or less based on 100 parts by mass, the total of the chloroprene (A-1) and the 2,3-dichloro-1,3-butadiene (A-2). By setting the use amount to 10 parts by mass or less, the tensile strength or the tensile elongation at break of the chloroprene copolymer is improved and the stability of flexibility with time is satisfactorily held.

Although a method for polymerizing the chloroprene copolymer is not particularly limited, emulsion polymerization can be adopted and aqueous emulsion polymerization is industrially preferable. By performing emulsion polymerization of the chloroprene (A-1), the 2,3-dichloro-1,3-butadiene (A-2), and the sulfur (A-3), the chloroprene copolymer latex (A) is obtained in which the particles of the chloroprene copolymer are dispersed, for example, in water. The obtained chloroprene copolymer latex (A) contains an emulsifier. As the emulsifier for the emulsion polymerization, common rosin acid soap is usable due to the simplicity of a solidification operation. In particular, sodium salt and/or potassium salt of disproportionated rosin acid are/is preferable from the viewpoint of coloring stability.

The use amount of the emulsifier containing rosin acid soap to the chloroprene copolymer latex (A) is preferably 3 parts by mass or more and 8 parts by mass or less when the total of all monomers of the chloroprene (A-1), the 2,3-dichloro-1,3-butadiene (A-2), the sulfur (A-3), the other monomers (A-4), and the like is set to 100 parts by mass. When the use amount is 3 parts by mass or more, poor emulsification is hard to occur and further the generation of heat by the polymerization can be suppressed and problems of the generation of aggregates and poor product appearance are hard to occur. Meanwhile, when the use amount is 8 parts by mass or less, the emulsifier, such as rosin acid, is hard to remain in the chloroprene copolymer, and therefore adhesion is hard to occur in the chloroprene copolymer. Hence, a deterioration of the processability and the operability due to the adhesion of the chloroprene copolymer to a mold (former) in the molding of the chloroprene copolymer latex composition, the adhesion of the molded product in use, or the like is hard to occur and further a deterioration of the color tone of the molded product is hard to occur.

As a polymerization initiator, common radical polymerization initiators are usable. For example, in a case of the emulsion polymerization, organic or inorganic peroxides, such as benzoyl peroxide, potassium persulfate, ammonium persulfate, cumene hydroperoxide, and t-butyl hydroperoxide, and azo compounds, such as azobisisobutyronitrile, are used. The polymerization initiators may be used alone or in combination of two or more types.

In the polymerization of the chloroprene copolymer, promoters may be used as desired in combination with the polymerization initiator. The promoters usable in combination with the polymerization initiator are not particularly limited and general promoters are usable. For example, anthraquinone sulfonate, potassium sulfite, sodium disulfite, sodium sulfite, tetraethylene pentamine, N,N-dimethyl-p-toluidine are mentioned. The promotors may be used alone or in combination of two or more types.

In general, in the manufacturing of the chloroprene polymer, when a predetermined polymerization rate is reached, a polymerization terminator is added to stop the polymerization reaction for the purpose of obtaining a polymer having desired molecular weight and molecular weight distribution. Also in this embodiment, the polymerization terminator may also be used. The type of the polymerization terminator is not particularly limited and commonly used polymerization terminators, e.g., phenothiazine, p-t-butylcatechol, hydroquinone, hydroquinone monomethyl ether, diethyl hydroxylamine, and the like, are usable. The polymerization terminators may be used alone or in combination of two or more types.

Further, the chloroprene polymer is generally susceptible to a deterioration by oxygen. Hence, stabilizers, such as an acid acceptor and an antioxidant, may be compounded in the chloroprene copolymer latex (A) insofar as the objects of the present invention are not impaired.

The degree of polymerization conversion in polymerization of the chloroprene copolymer is not particularly limited and is preferably 95% or more and more preferably 98% or more. When the degree of polymerization conversion is 95% or more, the amount of unreacted sulfur (A-3) is small, and therefore the physical properties of the molded product are hard to fluctuate. Further, when the amount of the unreacted sulfur (A-3) is small, the storage stability of the chloroprene copolymer latex (A) is excellent, which results in the fact that the storage stability of the chloroprene copolymer latex composition is excellent.

[3] Content of Tetrahydrofuran Insoluble Content in Chloroprene Copolymer

The content of the tetrahydrofuran insoluble content in the chloroprene copolymer is 50% by mass or more and 85% by mass or less. The content of the tetrahydrofuran insoluble content is controlled by the content of the sulfur (A-3) and the degree of polymerization conversion. When the content of the tetrahydrofuran insoluble content is 50% by mass or more, the tensile strength of the molded product of the chloroprene copolymer latex composition increases and the adhesion of the chloroprene copolymer to a mold is hard to occur, so that the chloroprene copolymer is likely to peel in the molding of the chloroprene copolymer latex composition.

Meanwhile, when the content of the tetrahydrofuran insoluble content in the chloroprene copolymer is 85% by mass or less, the chloroprene copolymer becomes tough and the flexibility, the tensile strength, and the tensile elongation at break of the molded product are excellent.

In order to further improve such effects, the content of the tetrahydrofuran insoluble content in the chloroprene copolymer is preferably set to 60% by mass or more and 85% by mass or less.

[4] Chloroprene Copolymer Latex Composition

The chloroprene copolymer latex composition according to this embodiment is a composition containing at least the chloroprene copolymer latex (A), the metal oxide (B), the vulcanization accelerator (C), and the antioxidant (D). Since the metal oxide (B), the vulcanization accelerator (C), and the antioxidant (D) are contained, a chloroprene copolymer latex composition capable of forming a molded product having sufficient tensile strength find flexibility is obtained. When any of the metal oxide (B), the vulcanization accelerator (C), and the antioxidant (D) is insoluble in water or destabilizes the colloidal state of the chloroprene copolymer latex (A), any of the metal oxide (B), the vulcanization accelerator (C), and the antioxidant (D) may be prepared into a dispersion in which any of the metal oxide (B), the vulcanization accelerator (C), or the antioxidant (D) is dispersed in water in advance, and then the dispersion may be mixed with the chloroprene copolymer latex (A).

The amount of each of the metal oxide (B), the vulcanization accelerator (C), and the antioxidant (D) contained in the chloroprene copolymer latex composition according to this embodiment is as follows. More specifically, when the amount of the solid content in the chloroprene copolymer latex (A) is set to 100 parts by mass, the amount of the metal oxide (B) contained in the chloroprene copolymer latex composition according to this embodiment is 1 part by mass or more and 10 parts by mass or less, the amount of the vulcanization accelerator (C) contained in the chloroprene copolymer latex composition is 0.1 part by mass or more and 5 parts by mass or less, and the amount of the antioxidant (D) contained in the chloroprene copolymer latex composition is 0.1 part by mass or more and 5 parts by mass or less.

The type of the metal oxide (B) is not particularly limited. For example, zinc oxide, lead oxide, and trilead tetraoxide are usable and zinc oxide is particularly preferable. The metal oxides (B) may be used alone or in combination of two or more types.

The amount of the metal oxide (B) contained in the chloroprene copolymer latex composition according to this embodiment is 1 part by mass or more and 10 parts by mass or less when the amount of the solid content in the chloroprene copolymer latex (A) is set to 100 parts by mass. When the amount of the metal oxide (B) is in the range above, a proper crosslinking speed is obtained, so that crosslinking deficiency or scorching is hard to occur. Further, the colloidal state of the chloroprene copolymer latex composition is stabilized, and therefore a problem, such as sedimentation, is hard to occur.

The type of the vulcanization accelerator (C) is not particularly limited and those generally used for the vulcanization of a chloroprene-based polymer latex are usable. For example, thiuram-based, dithiocarbamate-based, thiourea-based, and guanidinium-based vulcanization accelerators are mentioned.

Examples of the thiuram-based vulcanization accelerators include tetraethyl thiuram disulfide, tetrabutyl thiuram disulfide, and the like. Examples of the dithiocarbamate-based vulcanization accelerators include sodium dibutyldithiocarbamate, zinc dibutyldithiocarbamate, zinc diethyldithiocarbamate, and the like. Examples of the thiourea-based vulcanization accelerators include ethylenethiourea, diethylthiourea, trimethylthiourea, N,N'-diphenylthiourea (DPTU), and the like. Examples of the guanidinium-based vulcanization accelerators include diphenylguanidine (DPG), di-o-tolylguanidine, and the like. The vulcanization accelerators (C) may be used alone or in combination of two or more types.

The amount of the vulcanization accelerator (C) contained in the chloroprene copolymer latex composition according to this embodiment is 0.1 part by mass or more and 5 parts by mass or less when the amount of the solid content in the chloroprene copolymer latex (A) is set to 100 parts by mass. When the amount of the vulcanization accelerator (C) is in the range above, a proper crosslinking speed is obtained, so that crosslinking deficiency or scorching is hard to occur. Further, the crosslinking density of the molded product of the chloroprene copolymer latex composition according to this embodiment is also proper, and therefore proper flexibility can be imparted to the molded product. In order to further improve such effects, the amount of the vulcanization accelerator (C) is more preferably set to 0.5 part by mass or more and 1.5 parts by mass or less.

The type of the antioxidant (D) is not particularly limited. When high heat resistance is required, it is preferable to use an antioxidant preventing aging by heat and an antioxidant preventing aging by ozone in combination.

Examples of the antioxidant preventing the aging by heat include diphenylamine-based antioxidants, such as octylated diphenylamine, p-(p-toluenesulfonylamide)diphenylamine, and 4,4'-bis(α,α-dimethylbenzyl)diphenylamine. Such antioxidants can impart not only heat resistance but contamination resistance (suppression of discoloration or the like).

Examples of the antioxidant preventing the aging by ozone include N,N'-diphenyl-p-phenylenediamine (DPPD) and N-isopropyl-N'-phenyl-p-phenylenediamine (IPPD).

However, when the molded product of the chloroprene copolymer latex composition according to this embodiment is used as medical gloves, the appearance (particularly color tone) and hygiene of the molded product are emphasized, and therefore hindered phenol-based antioxidants are preferably used as the antioxidant (D).

The amount of the antioxidant (D) contained in the chloroprene copolymer latex composition according to this embodiment is 0.1 part by mass or more and 5 parts by mass or less when the amount of the solid content in the chloroprene copolymer latex (A) is set to 100 parts by mass. When the amount of the antioxidant (D) is in the range above, a sufficient antioxidant effect is obtained and an inhibition of crosslinking or a deterioration of the color tone is hard to occur.

The chloroprene copolymer latex composition according to this embodiment may contain, as desired, other additives other than the chloroprene copolymer latex (A), the metal oxide (B), the vulcanization accelerator (C), and the antioxidant (D) insofar as the objects of the present invention are not impaired. Examples of compoundable additives include pH adjusters, fillers, pigments, colorants, antifoaming agents, and thickeners, for example.

[5] Method for Manufacturing Molded Product of Chloroprene Copolymer Latex Composition By molding the chloroprene copolymer latex composition according to this embodiment, a molded product can be obtained. For example, a dipped product can be obtained by performing the molding by a dip processing method. For example, a film-like molded product is obtained by dipping a mold in the chloroprene copolymer latex composition according to this embodiment, solidifying the chloroprene copolymer on the surface of the mold, and then performing steps of leaching (removal of water-soluble impurities), drying, and vulcanization (crosslinking) in this order.

With respect to the vulcanization temperature (crosslinking temperature) in the vulcanization step (crosslinking step), a conventional chloroprene-based polymer latex has required a higher temperature (120 to 140° C.) than that in natural rubber. However, in the chloroprene copolymer latex composition according to this embodiment, the vulcanization temperature can be set to a lower temperature than that in the conventional one described above. Hence, the molded product can be manufactured at a lower energy cost than that in the conventional one.

For example, the vulcanization temperature (crosslinking temperature) in the vulcanization step (crosslinking step) can be set to 100° C. or more and 110° C. or less. The vulcanization time (crosslinking time) in the vulcanization temperature (crosslinking temperature) can be set to 20 minutes or more and 60 minutes or less, for example. However, the vulcanization is preferably sufficiently performed in the range where the tensile strength or the tensile elongation at break of the molded product does not deteriorate. For the purpose of avoiding a problem of the appearance of the molded product, e.g., generation of blister, pinhole, and the like, rough drying may be performed in advance at a relatively low temperature of 70° C. or more and 100° C. or less before the vulcanization step (crosslinking step).

As described above, the molded product can be obtained in which the 300% modulus of elasticity is 0.5 MPa or more and 1.6 MPa or less, the tensile strength is 18 MPa or more (more preferably 20 MPa or more), and the tensile elongation at break is 800% or more. The 300% modulus of elasticity serves as the index of flexibility. The 300% modulus of elasticity of a smaller value indicates that the flexibility is higher. The molded product obtained by molding the chloroprene copolymer latex composition according to this embodiment has excellent flexibility.

EXAMPLES

The present invention is described in more detail by giving Examples and Comparative Examples.

Example 1

(1) Preparation of Chloroprene Copolymer Latex (A)

In a reactor having an internal volume of 5 L, 1355 g of chloroprene, 145 g of 2,3-dichloro-1,3-butadiene, 3.8 g of sulfur, 1290 g of pure water, 36 g of rosin acid (Rosin HTR manufactured by Arakawa Chemical Industries, Ltd.), 57.8 g of potassium hydroxide, 29.7 g of sodium hydroxide, 15 g of sodium salt of β-naphthalene sulfonic acid formalin condensate, and 11.7 mg of copper sulfate were charged and emulsified, thereby forming the rosin acid into as a rosin soap.

The chloroprene, the 2,3-dichloro-1,3-butadiene, and the sulfur were compounded as raw material monomers and the pure water was compounded as a dispersion medium of emulsion polymerization. Further, the rosin acid, the potassium hydroxide, and the sodium hydroxide were compounded as raw materials of an emulsifier. The sodium salt of β-naphthalene sulfonic acid formalin condensate was compounded as an emulsifier. The copper sulfate was compounded as a promoter for the emulsion polymerization.

To the emulsified substance, 4 g of potassium persulfate was added as a polymerization initiator, and then emulsion polymerization was performed at 40° C. for 5 hours under a nitrogen gas atmosphere. Thereafter, the temperature was increased to 45° C., and then the polymerization was continued for 1 hour. After the lapse of 6 hours in total after the start of the polymerization, the polymerization was stopped. Subsequently, unreacted chloroprene and 2,3-dichloro-1,3-butadiene were removed by steam distillation, thereby obtaining the chloroprene copolymer latex (A).

The degree of polymerization conversion was calculated as follows. The emulsified substance after the polymerization was collected, and then dried at 141° C. for 30 minutes, thereby obtaining dried solid matter. The degree of polymerization conversion was calculated by the expression below using a value obtained by subtracting the mass of the solid content other than a polymer from the mass of the dried solid matter as the "generation amount of chloroprene copolymer". The mass of the solid content other than the polymer was calculated by determining a component not volatilizing at 141° C. from various components used for the emulsion polymerization. The calculated degree of polymerization conversion is shown in Table 1.

Degree of polymerization conversion [%]=[(Generation amount of chloroprene copolymer)/(Total charged mass of all monomers)]×100

Further, the solid content concentration of the chloroprene copolymer latex (A) was calculated as follows. The chloroprene copolymer latex (A) was dried at 100° C. for 2 hours to give dried solid matter. Then, the mass of the dried solid matter was measured, and then the solid content concentration was calculated from the ratio of the mass of the dried solid matter to the mass of the chloroprene copolymer latex (A) before the drying (see the following expression).

Solid content concentration [mass %]=[(Mass after drying)/(Mass before drying)]×100

Further, the content of each of a part derived from the chloroprene, a part derived from the 2,3-dichloro-1,3-butadiene, and the sulfur in the obtained chloroprene copolymer was calculated from the degree of polymerization conversion. A method for calculating the content is described below. The calculated results are shown in Table 1.

The 2,3-dichloro-1,3-butadiene (A-2) are almost consumed to be polymerized at the early stage of the polymerization. The sulfur (A-3) remains in the polymer without volatilizing even if unreacted matter is present. Hence, only the chloroprene (A-1) is an unreacted monomer contributing to the degree of polymerization conversion, and therefore the content of each component in the chloroprene copolymer is approximately calculated by the expression below.

[Content (part by mass) of the part derived from the 2,3-dichloro-1,3-butadiene (A-2) when the total amount of the part derived from the chloroprene (A-1) and the part derived from the 2,3-dichloro-1,3-butadiene (A-2) in the chloroprene copolymer is set to 100 parts by mass]= [Charged amount (part by mass) of the 2,3-dichloro-1,3-butadiene (A-2)]/[Degree of polymerization conversion (%)]×100

[Content (part by mass) of the sulfur (A-3) when the total amount of the part derived from the chloroprene (A-1) and the part derived from the 2,3-dichloro-1,3-butadiene (A-2) in the chloroprene copolymer is set to 100 parts by mass]= [Charged amount (part by mass) of the sulfur (A-3)]/[Degree of polymerization conversion (%)]×100

Further, various physical properties of the obtained the chloroprene copolymer latex (A) were evaluated.

The content of a tetrahydrofuran insoluble content in the chloroprene copolymer was measured as follows. More specifically, 1 g of the chloroprene copolymer latex (A) was added dropwise to 100 mL of tetrahydrofuran, shaken overnight, and then subjected to centrifugation using a centrifugal separator to give a supernatant dissolved phase. The obtained dissolved phase was heated to 100° C. for the evaporation of the tetrahydrofuran to be dried and solidified for 1 hour, and then the mass of dried solid matter was measured Thus, the mass of the dissolved content dissolved in the dissolved phase of the chloroprene copolymers is obtained.

Then, the mass of the chloroprene copolymer in 1 g of the chloroprene copolymer latex (A) and the mass of the dissolved content were substituted into the expression below, thereby calculating the content of the tetrahydrofuran insoluble content not dissolved in the tetrahydrofuran of the chloroprene copolymer. The measured content of the tetrahydrofuran insoluble content is shown in Table 1.

Content (%) of tetrahydrofuran insoluble content={1−[(Mass of dissolved content)/(Mass of chloroprene copolymer in 1 g of chloroprene copolymer latex (A))]}×100

Further, the storage stability of the chloroprene copolymer latex (A) was evaluated as follows. The chloroprene copolymer latex (A) placed in an airtight container was heated in a 70° C. oven for 168 hours, and then the amount of an alkali residue in the chloroprene copolymer latex (A) was measured. The measurement of the amount of the alkali residue was performed by neutralization titration using hydrochloric acid having a concentration of ⅓ mol/L. Then, a case where the reduction rate of the amount of the alkali residue is lower than that before the heating is determined that the storage stability is excellent. The evaluation results of the storage stability are shown in Table 1. A case where the reduction rate of the amount of the alkali residue is 60% or less is determined that the storage stability is excellent and is marked with a ○ mark in Table 1. A case where the reduction rate of the amount of the alkali residue exceeds 60% is determined that the storage stability is insufficient and is marked with a x mark in Table 1.

(2) Preparation of Chloroprene Copolymer Latex Composition

The chloroprene copolymer latex (A) obtained in (1) above, zinc oxide AZ-SW manufactured by OSAKI INDUSTRY CO., LTD., a vulcanization accelerator NOCCELLAR C (diphenylthiourea) manufactured by OUCHI SHINKO CHEMICAL INDUSTRIAL CO., LTD., a vulcanization accelerator NOCCELLAR D (diphenylguanidine) manufactured by OUCHI SHINKO CHEMICAL INDUSTRIAL CO., LTD., and a phenolic antioxidant Selosol L-306-40 manufactured by CHUKYO YUSHI CO., LTD. were charged in a container with a stirring device. Then, stirring was performed for 5 minutes for uniform mixing to give a chloroprene copolymer latex composition. The chloroprene copolymer latex composition after stirred was allowed to stand still at room temperature (20° C.) for 24 hours to be matured.

With respect to the charged amount of each of the zinc oxide AZ-SW, the vulcanization accelerator NOCCELLAR C, the vulcanization accelerator NOCCELLAR D, and the phenolic antioxidant Selosol L-306-40, the zinc oxide AZ-SW is 5 parts by mass, the vulcanization accelerator NOCCELLAR C is 2 parts by mass, the vulcanization accelerator NOCCELLAR D is 1 part by mass, and the phenolic antioxidant Selosols L-306-40 is 2 parts by mass when the amount of the solid content in the charged chloroprene copolymer latex (A) is set to 100 parts by mass.

However, the zinc oxide AZ-SW and the phenolic antioxidant Selosol L-306-40 have dispersion forms in which zinc oxide and an antioxidant, respectively, which are active components are dispersed in liquid media, and therefore the charged amounts of the zinc oxide AZ-SW and the phenolic antioxidant Selosol L-306-40 described above are the amounts of only the active components of the charged zinc oxide AZ-SW and phenolic antioxidant Selosol L-306-40.

(3) Production of Film

A film of a chloroprene copolymer was molded by a dip processing method using the chloroprene copolymer latex composition obtained in (2) above. As a mold of the film of the chloroprene copolymer, a ceramic plate 200 mm in length, 100 mm in width, and 5 mm in thickness was prepared. The mold was dipped in 30% by mass of an aqueous calcium nitrate solution, pulled up, and then dried in a 40° C. oven for 5 minutes, whereby the calcium nitrate which is a coagulant was caused to adhere to the surface of the mold.

Further, the dried mold was dipped in the chloroprene copolymer latex composition obtained in (2) above, so that a film was formed on the surface of the mold. The mold was pulled up from the chloroprene copolymer latex composition, and then dried in a 70° C. oven for 30 minutes.

Next, the mold having the film formed on the surface was heated at 110° C. for 30 minutes in an oven to be vulcanized (crosslinking reaction) and cured. After allowed to cool under the atmosphere, the film was cut out from the surface of the mold to give a film of the crosslinked chloroprene copolymer.

The crosslinked film was cut to give a specimen of a dumbbell shape No. 6 as defined in JIS K6251. The thickness of the specimen was 0.15 to 0.25 mm. The specimen was heat-treated at 110° C. for 16 hours in the air to be subjected to heat aging treatment. The specimen before and after the heat aging treatment was measured for the tensile strength, the tensile elongation at break, and the modulus of elasticity at 300% elongation (300% modulus of elasticity) by performing a tensile test under room temperature by a method according to JIS K6301. The various physical properties of the film measured as described above are collectively shown in Table 1.

TABLE 1

| | | Ex. 1 | Ex. 2 | Ex. 3 | Ex. 4 | Ex. 5 | Comp. Ex. 1 |
|---|---|---|---|---|---|---|---|
| Polymerization conditions | Use amount of chloroprene (A-1) (part by mass) | 90.3 | 85.6 | 85.6 | 90.3 | 90.3 | 91.75 |
| | Use amount of 2,3-dichloro-1,3-butadiene (A-2) (part by mass) | 9.7 | 14.4 | 14.4 | 9.7 | 9.7 | 8.25 |
| | Use amount of sulfur (A-3) (part by mass) | 0.25 | 0.25 | 0.25 | 0.25 | 0.75 | 0 |
| | Use amount of rosin acid (part by mass) | 2.4 | 2.4 | 2.4 | 3.4 | 3.4 | 4.3 |
| | Polymerization temperature (° C.) | 40-45 | 40-45 | 40-45 | 40-45 | 40-45 | 40 |
| | Degree of polymerization conversion (%) | 98 | 98 | 98 | 98 | 95 | 90 |
| Contents in chloroprene copolymer | Part derived from chloroprene (part by mass) | 91.2 | 85.3 | 85.3 | 90.1 | 89.8 | 90.8 |
| | Part derived from 2,3-dichloro-1,3-butadiene (part by mass) | 9.8 | 14.7 | 14.7 | 9.9 | 10.2 | 9.2 |
| | Sulfur (part by mass) | 0.26 | 0.26 | 0.26 | 0.26 | 0.79 | 0 |
| Compound ratios of compositions (part by mass) | Chloroprene copolymer latex (A) | 100 | 100 | 100 | 100 | 100 | 100 |
| | Metal oxide (B): Zinc oxide | 5 | 5 | 5 | 5 | 5 | 5 |
| | Vulcanization accelerator: NOCCELLAR C | 2 | 2 | 0.25 | 1 | 1 | 2 |
| | Vulcanization accelerator: NOCCELLAR D | 1 | 1 | 1 | 0 | 0 | 1 |
| | Vulcanization accelerator: NOCCELLAR BZ | 0 | 0 | 0 | 1 | 1 | 0 |
| | Antioxidant (D): Phenolic antioxidant | 2 | 2 | 2 | 1 | 1 | 2 |
| Vulcanization conditions | Temperature (° C.) | 110 | 110 | 110 | 110 | 110 | 110 |
| | Time (min) | 30 | 30 | 30 | 30 | 30 | 30 |
| Evaluations | Tetrahydrofuran insoluble content (% by mass) | 70 | 72 | 62 | 77 | 5 | 40 |
| | Modulus of elasticity at 300% before heat aging treatment (MPa) | 1.5 | 1.6 | 1.0 | 1.2 | 1.4 | 1.0 |
| | Tensile strength before heat aging treatment (MPa) | 24 | 24 | 24 | 18 | 26 | 16 |

TABLE 1-continued

|  |  |  |  |  |  |  |  |
|---|---|---|---|---|---|---|---|
| Tensile elongation at break before heat aging treatment (%) | 1000 | 1000 | 1125 | 1000 | 1025 | 1125 |
| Modulus of elasticity at 300% after heat aging treatment (MPa) | 2.0 | 2.3 | 1.4 | 2.0 | 2.2 | 1.7 |
| Tensile strength before after aging treatment (MPa) | 14 | 6 | 27 | 17 | 18 | 20 |

| | | Comp. Ex. 2 | Comp. Ex. 3 | Comp. Ex. 4 | Comp. Ex. 5 | Comp. Ex. 6 |
|---|---|---|---|---|---|---|
| Polymerization conditions | Use amount of chloroprene (A-1) (part by mass) | 100 | 85.6 | 91.75 | 91.75 | 91.75 |
| | Use amount of 2,3-dichloro-1,3-butadiene (A-2) (part by mass) | 0 | 14.4 | 8.25 | 8.25 | 8.25 |
| | Use amount of sulfur (A-3) (part by mass) | 0.25 | 1.5 | 0 | 0 | 0 |
| | Use amount of rosin acid (part by mass) | 3.4 | 2.4 | 4.3 | 4.3 | 4.3 |
| | Polymerization temperature (° C.) | 40-45 | 40-45 | 40 | 40 | 40 |
| | Degree of polymerization conversion (%) | 99 | 85 | 90 | 90 | 90 |
| Contents in chloroprene copolymer | Part derived from chloroprene (part by mass) | 100 | 83.1 | 90.8 | 90.8 | 90.8 |
| | Part derived from 2,3-dichloro-1,3-butadiene (part by mass) | 0 | 16.9 | 9.2 | 9.2 | 9.2 |
| | Sulfur (part by mass) | 0.25 | 1.76 | 0 | 0 | 0 |
| Compound ratios of compositions (part by mass) | Chloroprene copolymer latex (A) | 100 | — | 100 | 100 | 100 |
| | Metal oxide (B): Zinc oxide | 5 | — | 5 | 5 | 5 |
| | Vulcanization accelerator: NOCCELLAR C | 2 | — | 2 | 0 | 0 |
| | Vulcanization accelerator: NOCCELLAR D | 1 | — | 1 | 1 | 1 |
| | Vulcanization accelerator: NOCCELLAR BZ | 0 | — | 0 | 1 | 1 |
| | Antioxidant (D): Phenolic antioxidant | 2 | — | 2 | 1 | 1 |
| Vulcanization conditions | Temperature (° C.) | 110 | — | 120 | 110 | 130 |
| | Time (min) | 30 | — | 45 | 30 | 30 |
| Evaluations | Tetrahydrofuran insoluble content (% by mass) | 65 | Less than 1 | 40 | 40 | 40 |
| | Modulus of elasticity at 300% before heat aging treatment (MPa) | 1.7 | — | 1.1 | 0.7 | 0.9 |
| | Tensile strength before heat aging treatment (MPa) | 26 | — | 18 | 12 | 18 |
| | Tensile elongation at break before heat aging treatment (%) | 750 | — | 1000 | 900 | 775 |
| | Modulus of elasticity at 300% after heat aging treatment (MPa) | 2.3 | — | 1.7 | — | — |
| | Tensile strength before after aging treatment (MPa) | 20 | — | 26 | — | — |

Example 2

A chloroprene copolymer latex (A), a chloroprene copolymer latex composition, a film, and a specimen were produced completely in the same manner as in Example 1, except changing the use amount of the 2,3-dichloro-1,3-butadiene as shown in Table 1 to prepare the chloroprene copolymer latex (A) and various evaluations were performed in the same manner as in Example 1. The results are shown in Table 1.

Example 3

A chloroprene copolymer latex (A), a chloroprene copolymer latex composition, a film, and a specimen were produced completely in the same manner as in Example 1, except changing the use amount of the 2,3-dichloro-1,3-butadiene as shown in Table 1 to prepare the chloroprene copolymer latex (A) and changing the use amount of the vulcanization accelerator NOCCELLAR C as shown in Table 1 to prepare the chloroprene copolymer latex composition and various evaluations were performed in the same manner as in Example 1. The results are shown in Table 1.

Examples 4 and 5

Chloroprene copolymer latexes (A), chloroprene copolymer latex compositions, films, and specimens were produced completely in the same manner as in Example 1, except changing the use amount of the rosin acid as shown in Table 1 to prepare the chloroprene copolymer latexes (A) and changing the type and the use amount of the vulcanization accelerator and the use amount of the antioxidant as shown in Table 1 to prepare the chloroprene copolymer latex compositions and various evaluations were performed in the same manner as in Example 1. The results are shown in Table 1. A vulcanization accelerator (C) NOCCELLAR BZ in Table 1 is a vulcanization accelerator NOCCELLAR BZ (zinc dibutyl carbamate) manufactured by OUCHI SHINKO CHEMICAL INDUSTRIAL CO., LTD.

Comparative Examples 1 to 3

Chloroprene copolymer latexes (A), chloroprene copolymer latex compositions, films, and specimens were produced completely in the same manner as in Example 1, except changing the use amount of each of the 2,3-dichloro-1,3-butadiene, the sulfur, and the rosin acid as shown in Table 1 to prepare the chloroprene copolymer latexes (A) and various evaluations were performed in the same manner as in Example 1. The results are shown in Table 1.

Comparative Example 4

A chloroprene copolymer latex (A), a chloroprene copolymer latex composition, a film, and a specimen were produced completely in the same manner as in Comparative Example 1, except changing the vulcanization conditions of the film to 120° C. and 45 minutes (conventional vulcanization conditions) and various evaluations were performed in the same manner as in Example 1. The results are shown in Table 1.

Comparative Example 5

A chloroprene copolymer latex (A), a chloroprene copolymer latex composition, a film, and a specimen were produced completely in the same manner as in Comparative Example 1, except changing the type and the use amount of the vulcanization accelerator and the use amount of the antioxidant as shown in Table 1 to prepare the chloroprene copolymer latex composition and various evaluations were performed in the same manner as in Example 1. The results are shown in Table 1.

Comparative Example 6

A chloroprene copolymer latex (A), a chloroprene copolymer latex composition, a film, and a specimen were produced completely in the same manner as in Comparative Example 5, except changing the vulcanization conditions of the film to 130° C. and 30 minutes and various evaluations were performed in the same manner as in Example 1. The results are shown in Table 1.

In Examples 1 to 3, the sulfur was added in the preparation of the chloroprene copolymer latexes (A), and therefore the films having high mechanical strength were obtained even when the vulcanization was per formed under a temperature condition lower than before as compared with Comparative Example 1 in which no sulfur was added. Further, a comparison between Examples 4 and 5 shows that the tensile strength of the film of the crosslinked chloroprene copolymer is higher when the use amount of the sulfur is larger.

In Comparative Example 3, the compounding amount of the sulfur was large, and therefore, while the content of the tetrahydrofuran insoluble content was low and the flexibility of the film was improved, the storage stability of the chloroprene copolymer latex (A) was low.

Further, a comparison between Examples 1 to 3 and Comparative Example 2 shows that the flexibility of the films is improved by the use of the 2,3-dichloro-1,3-butadiene. Further, a comparison between Comparative Examples 5 and 6 shows that, when sulfur was not used, a difference occurs in the tensile strength, the tensile elongation at break, and the 300% modulus of elasticity of the films of the crosslinked chloroprene copolymers due to a difference in the vulcanization temperature.

The invention claimed is:

1. A chloroprene copolymer latex composition comprising:
    a chloroprene copolymer latex (A), a metal oxide (B), a vulcanization accelerator (C), and an antioxidant (D), wherein
    the chloroprene copolymer latex (A) is a latex containing particles of a chloroprene copolymer which is a copolymer of chloroprene (A-1), 2,3-dichloro-1,3-butadiene (A-2), and sulfur (A-3),
    a content of the sulfur (A-3) in the chloroprene copolymer is 0.1 part by mass or more and 1.0 part by mass or less when a total amount of the chloroprene (A-1) and the 2,3-dichloro-1,3-butadiene (A-2) is set to 100 parts by mass, and
    a content of a tetrahydrofuran insoluble content in the chloroprene copolymer is 50% by mass or more and 85% by mass or less.

2. The chloroprene copolymer latex composition according to claim 1, wherein
    a copolymerization ratio of the chloroprene (A-1) is 76% by mass or more and 93% by mass or less and a copolymerization ratio of the 2,3-dichloro-1,3-butadiene (A-2) is 24% by mass or less and 7% by mass or more when the total amount of the chloroprene (A-1) and the 2,3-dichloro-1,3-butadiene (A-2) is set to 100% by mass.

3. The chloroprene copolymer latex composition according to claim 1, wherein
    when an amount of a solid content in the chloroprene copolymer latex (A) is set to 100 parts by mass, an amount of the metal oxide (B) is 1 part by mass or more and 10 parts by mass or less, an amount of the vulcanization accelerator (C) is 0.1 part by mass or more and 5 parts by mass or less, and an amount of the antioxidant (D) is 0.1 part by mass or more and 5 parts by mass or less.

4. A molded product, which is the chloroprene copolymer latex composition according to claim 1, wherein
    a 300% modulus of elasticity is 0.5 MPa or more and 1.6 MPa or less, a tensile strength is 18 MPa or more, and a tensile elongation at break is 800% or more.

5. The molded product according to claim 4, which is a dipped product.

6. The molded product according to claim 5, which is a glove.

7. The molded product according to claim 5, which is a medical disposable glove.

8. The chloroprene copolymer latex composition according to claim 2, wherein
    when an amount of a solid content in the chloroprene copolymer latex (A) is set to 100 parts by mass, an amount of the metal oxide (B) is 1 part by mass or more and 10 parts by mass or less, an amount of the vulcanization accelerator (C) is 0.1 part by mass or more and 5 parts by mass or less, and an amount of the antioxidant (D) is 0.1 part by mass or more and 5 parts by mass or less.

9. A molded product, which is the chloroprene copolymer latex composition according to claim 2, wherein
    a 300% modulus of elasticity is 0.5 MPa or more and 1.6 MPa or less, a tensile strength is 18 MPa or more, and a tensile elongation at break is 800% or more.

10. A molded product, which is the chloroprene copolymer latex composition according to claim 3, wherein
    a 300% modulus of elasticity is 0.5 MPa or more and 1.6 MPa or less, a tensile strength is 18 MPa or more, and a tensile elongation at break is 800% or more.

11. The chloroprene copolymer latex composition according to claim 1, wherein particles of the chloroprene copolymer are dispersed in water.

12. A method of producing a chloroprene copolymer latex composition comprising:
    adding chloroprene (A-1), 2,3-dichloro-1,3-butadiene (A-2) and sulfur (A-3) to obtain chloroprene copolymer latex (A) containing particles of a chloroprene copolymer, and
    stirring the chloroprene copolymer latex (A), a metal oxide (B), a vulcanization accelerator (C), and an antioxidant (D) to obtain the chloroprene copolymer latex composition,
    wherein a content of a tetrahydrofuran insoluble content in the chloroprene copolymer is 50% by mass or more and 85% by mass or less, and
    wherein a content of the sulfur (A-3) in the chloroprene copolymer is 0.1 part by mass or more and 1.0 part by mass or less when a total amount of the chloroprene (A-1) and the 2,3-dichloro-1,3-butadiene (A-2) is set to 100 parts by mass.

13. The method according to claim 12, wherein particles of the chloroprene copolymer are dispersed in water.

14. The method according to claim 12, wherein chloroprene (A-1), 2,3-dichloro-1,3-butadiene (A-2) and sulfur (A-3) are added at a same time.

* * * * *